US008729320B2

(12) United States Patent
Amii et al.

(10) Patent No.: US 8,729,320 B2
(45) Date of Patent: May 20, 2014

(54) METHOD FOR PRODUCING DIFLUOROCYCLOPROPANE COMPOUND

(75) Inventors: Hideki Amii, Kobe (JP); Kojun Oshiro, Kobe (JP); Yoshimichi Morimoto, Kobe (JP); Makoto Matsuura, Kawagoe (JP)

(73) Assignee: Central Glass Company, Limited, Ube-Shi (JP)

( * ) Notice: Subject to any disclaimer, the term of this patent is extended or adjusted under 35 U.S.C. 154(b) by 132 days.

(21) Appl. No.: 13/520,691

(22) PCT Filed: Oct. 26, 2010

(86) PCT No.: PCT/JP2010/068932
§ 371 (c)(1),
(2), (4) Date: Jul. 5, 2012

(87) PCT Pub. No.: WO2011/083612
PCT Pub. Date: Jul. 14, 2011

(65) Prior Publication Data
US 2012/0277458 A1 Nov. 1, 2012

(30) Foreign Application Priority Data
Jan. 8, 2010 (JP) ................................. 2010-003201

(51) Int. Cl.
*C07C 23/04* (2006.01)
(52) U.S. Cl.
USPC .......................................... 570/133; 570/123
(58) Field of Classification Search
USPC .................................. 556/476; 570/123, 133
See application file for complete search history.

(56) References Cited

U.S. PATENT DOCUMENTS

| 3,825,606 | A | 7/1974 | O'Neill et al. |
| 3,903,181 | A | 9/1975 | O'Neill et al. |
| 3,906,111 | A | 9/1975 | Billings et al. |
| 3,928,468 | A | 12/1975 | Billings et al. |
| 4,201,881 | A | 5/1980 | DeLuca et al. |
| 5,089,662 | A * | 2/1992 | Wegner et al. ........... 562/506 |
| 6,051,539 | A | 4/2000 | Kodali et al. |
| 2009/0318408 | A1 * | 12/2009 | Cai et al. ............. 514/210.18 |

FOREIGN PATENT DOCUMENTS

| EP | 1 026 154 A2 | 8/2000 |
| JP | 49-48637 A | 5/1974 |
| JP | 50-126642 A | 10/1975 |
| JP | 56-500296 A | 3/1981 |
| JP | 5-78272 A | 3/1993 |
| JP | 2001-213830 A | 8/2001 |
| JP | 2001-213830 A | 8/2001 |
| JP | 2003-524593 A | 8/2003 |
| JP | 2003-524593 A | 8/2003 |
| JP | 2004-182671 A | 7/2004 |
| JP | 2004-182671 A | 7/2004 |

OTHER PUBLICATIONS

Bessard et al., "gem-Difluorocyclopropenes by [1+2] Cycloaddition Reactions Between Difluorocarbene and Acetylenes Having Terminal or Internal Triple Bonds", Tetrahedron, Aug. 26, 1991, vol. 47, No. 35, pp. 7323-7328.

Birchall et al., "Difluorocarbene", Proc. Chem. Soc., Feb. 1960, p. 81.
International Search Report issued in PCT/JP2010/068932 dated Jan. 18, 2011.
Kirsch, "Modern Fluoroorganic Chemistry: Synthesis, Reactivity, Applications", Wiley-VCH: 2004, Weinheim, Germany, pp. 135-141.
Kojun et al., "Sodium Bromodifluoroacetate: A Difluorocarbene Source for the Synthesis of gem-Difluorocyclopropanes", Synthesis, Jun. 16, 2010, No. 12, pp. 2080-2084.
Kojun et al., "Synthesis of Difluorocyclopropane Using a New Difluorocyclopropane source", 90th Annual Meeting of Chemical Society of Japan in Spring 2010 Nen Koen Yokoshu IV, Mar. 12, 2010, p. 1346.
Morimoto et al., "Synthesic Applications of Functionalyzed Difluorocyclopropanes" 87th Annual Meeting of Chemical Society of Japan in Spring 2007 Nen Koen Yokoshu II, Mar. 12, 2007, p. 904.
Ojima (Ed.), "Fluorine in Medicinal Chemistry and Chemical Biology", Wiley-Blackwell, 2009, London, UK, pp. 313-334.
Seyferth et al., "Halomethyl Metal Compounds. XIII. The Preparation of gem-Difluorocyclopropanes by Iodide Ion Induced CF2 Transfer from Trimethyl(trifluoromethyl)tin", J. Org. Chem., 1967, vol. 32, pp. 2980-2984.
Tian et al., "A Novel and Highly Efficient Synthesis of gem-Difluorocyclopropanes", Organic Letters, 2000, vol. 2, No. 4, pp. 563-564.
Tissot et al., "Thermal Decomposition of the Alkaline Salts of Difluorochloro-and Difluorobromoacetic Acids", Thermochimica Acta, 1983, 66, pp. 315-321.
Wu et al., "Application of carbene reactive intermediates in organic synthesis", ACTA Chimica Sinica English Edition, 1989, No. 3, pp. 253-257.
Xu et al., "3,3-Difluoro-1-iodocyclopropenes: A Simple Synthesis and Their Reactions", J. Org. Chem., 2002, 67, pp. 9421-9427.
Zafrani et al., "Diethyl bromodifluoromethylphosphonate: a highly efficient and environmentally benign difluorocarbene precursor", Tetrahedron, Jul. 4, 2009, vol. 65, No. 27, pp. 5278-5283.
Boyer et al., "Chemoselective and stereoselective synthesis of *gem*-difluoro-β-aminoesters or *gem*-difluoro-β-lactams from ethylbromodifluoroscetate and imines during Reformatsky reaction," Tetrahedron (2007), vol. 63, pp. 12352-12366.
Extended European Search Report issued Apr. 25, 2013, in European Patent Application No. 10842127.2.

* cited by examiner

*Primary Examiner* — Fereydoun G Sajjadi
*Assistant Examiner* — Pancham Bakshi
(74) *Attorney, Agent, or Firm* — Birch, Stewart, Kolasch & Birch, LLP

(57) ABSTRACT

Provided is a method for producing a difluorocyclopropane compound under milder reaction conditions and with high selectivity and high yield. The method for producing a difluorocyclopropane compound of the present invention is characterized by using sodium bromodifluoroacetate as a difluorocyclopropanation agent. With the disclosed method, a difluorocyclopropane compound can be produced under milder reaction conditions and with a higher conversion rate and a higher yield compared to conventional art. Further, by-products can be reduced significantly, thus allowing waste to be greatly reduced. Accordingly, the production method of the present invention is easy to implement industrially (can be employed on an industrial scale) and is thus extremely practical and useful.

6 Claims, No Drawings

METHOD FOR PRODUCING DIFLUOROCYCLOPROPANE COMPOUND

TECHNICAL FIELD

The present invention relates to a method for producing a difluorocyclopropane compound. Specifically, the present invention relates to a method for producing a difluorocyclopropane compound useful as an intermediate for pharmaceuticals or pesticides.

BACKGROUND ART

Recently, compounds having a difluorocyclopropane skeleton are attracting attention in the fields of pharmaceuticals and pesticides and materials chemistry (see Non-patent documents 1-2). For example, some of gem-difluorocyclopropane compounds have specific biological activities such as antitumor action and DNA cleaving action, and recently, introduction of a gem-difluorocyclopropane skeleton into molecules that make up living organisms such as nucleosides and amino acids, liquid crystals and polymer materials has been studied.

Further, for example, conversion into various difluoromethylene compounds utilizing ring cleavage reaction of difluorocyclopropanes has been studied. Thus, many applications using difluorocyclopropanes have been reported.

As methods for producing a difluorocyclopropane compound, methods for producing difluorocyclopropanes by means of thermal decomposition reaction using chlorodifluoroacetate (see Patent documents 1-2 and Non-patent document 3) and methods for producing difluorocyclopropanes using $PhHgCF_3$/NaI (see Non-patent document 4) are conventionally known.

Meanwhile, the generation of difluorocarbene species (: $CF_2$) in the reaction system at the time of synthesis of the difluorocyclopropane compound is conventionally and widely known, and for example, methods for generating the carbene species using various metal reagents (see Non-patent documents 5-7) are known.

PRIOR ART DOCUMENTS

Patent Documents

Patent document 1: Japanese National-phase PCT Laid-Open Patent Publication No. 2003-524593
Patent document 2: Japanese Laid-Open Patent Publication No. 2001-213830

Non-Patent Documents

Non-patent document 1: Ojima, I., Ed. Fluorine in Medicinal Chemistry and Chemical Biology; Wiley-Blackwell: London, UK, 2009; pp. 313-334
Non-patent document 2: Kirsh, P. Modern Fluoroorganic Chemistry: Synthesis, Reactivity, Applications; Wiley-VCH: Weinheim, Germany, 2004; pp. 135-141
Non-patent document 3: Birchall, J. M.; Cross, G. E.; Haszeldine, R. N. Proc. Chem. Soc. 1960,
Non-patent document 4: Wu, S.-H.; Yu, Q. Acta Chim. Sinica 1989, 253
Non-patent document 5: Tian, F.; Kruger, V. K.; Bautista, O.; Duan, J.-X.; Li, A.-R.; Dolbier, W. R., Jr.; Chen, Q.-Y. Org. Lett. 2000, 2, 563
Non-patent document 6: Xu, W.; Chen, Q.-Y. J. Org. Chem. 2002, 67, 9421
Non-patent document 7: Seyferth, D.; Dentouzos, H.; Zuzki, R.; Muy, J. Y.-P. J. Org. Chem. 1967, 32, 2980
Non-patent document 8: Tissot, P.; Waefler, J. P. Thermochim. Acta 1983, 66, 315

SUMMARY OF THE INVENTION

Problems to be Solved by the Invention

However, in the conventional methods using chlorodifluoroacetate (see Patent Documents 1-2 and Non-Patent Document 3), generation temperatures of difluorocarbene species from chlorodifluoroacetate are very high, and therefore, hot conditions (about 180° C.) are required for smooth progress of cycloaddition reaction. Further, in the conventional method using $PhHgCF_3$/NaI (Non-Patent Document 4), particularly a target product is easily decomposed under a hot condition, and therefore, it is very difficult to employ the method as a method using chlorodifluoroacetate.

Thus, the conventional methods of producing difluorocyclopropane compounds are not satisfactory.

The problem to be solved by the present invention is to provide a method for producing a difluorocyclopropane compound under milder reaction conditions and with high selectivity and high yield. In addition, the purpose of the invention is to provide a method for producing a difluorocyclopropane compound having various functional groups in which a post-treatment of a reaction is convenient (no hazardous waste is generated).

Means for Solving the Problems

The present inventors diligently made researches in order to solve the above-described problems. As a result, the present inventors found that when using sodium bromodifluoroacetate as a difluorocyclopropanation agent, it is possible to provide a method for producing a difluorocyclopropane compound with high selectivity and high yield that can solve the above-described problems.

In the conventional methods using chlorodifluoroacetate, conversion rates are not necessarily high (conversion rate: about 60%). When a difluorocyclopropane compound was actually produced, reaction progress became unsmooth in mid-course and in addition, it was very difficult to separate a target product from raw materials remaining in the reaction system. This is supported by the results that many by-products other than a target product tend to be easily produced obtained in experimental examples using sodium chlorodifluoroacetate (comparative examples described later).

Moreover, it is known that sodium bromodifluoroacetate tends to be thermally decomposed at a lower temperature when compared to sodium chlorodifluoroacetate (see Non-patent document 8).

Therefore, those skilled in the art naturally expected that even if sodium bromodifluoroacetate is used as a difluorocyclopropanation agent at the time of producing a difluorocyclopropane compound, the conversion rate and the yield would be low as in the case of using sodium chlorodifluoroacetate.

However, when the present inventors actually carried out the production of a difluorocyclopropane compound using sodium bromodifluoroacetate, surprisingly, it was found that a target product can be obtained with a significantly higher selectivity (conversion rate) and yield when compared to the case of using sodium chlorodifluoroacetate.

Further, the present inventors also found that a target product can be obtained with a higher yield when performing a reaction using sodium bromodifluoroacetate under specific reaction conditions.

More specifically, the present invention is as follows:

a method for producing a difluorocyclopropane compound by reacting a compound having a chain or cyclic ethylene skeleton or a derivative thereof with a difluorocyclopropanation agent, wherein bromodifluoroacetate is used as the difluorocyclopropanation agent.

In the production method of the present invention, examples of the compound having the ethylene skeleton or the derivative thereof include a compound represented by the following general formula (1):

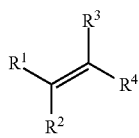

(1)

wherein in the general formula (1): $R^1$ to $R^4$ each independently represent a hydrogen atom, or a $C_{1-10}$ linear or branched aliphatic hydrocarbon group, aromatic ring group, alkoxy group, alkoxycarbonyl group, trialkylsilyl group or boryl group, which may be substituted with any group; and $R^2$ and $R^4$ may mutually constitute a portion of the same aliphatic ring or aliphatic heterocycle, or may mutually form a single bond, and examples of the difluorocyclopropane compound include a compound represented by the following general formula (2):

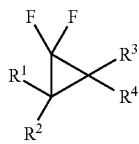

(2)

wherein in the general formula (2), $R^1$ to $R^4$ are the same as above.

Further, in the production method of the present invention, examples of the bromodifluoroacetate include those represented by the following formula:

$BrCF_2CO_2R^5$ wherein $R^5$ represents an alkali metal atom or an alkali earth metal atom. In this regard, examples of the alkali metal include sodium, lithium and potassium, and examples of the alkali earth metal include magnesium.

Moreover, in the production method of the present invention, a reaction temperature of the reaction may be, for example, 100 to 200° C., and a reaction time of the reaction may be, for example, 5 to 60 minutes.

Effect of the Invention

According to the present invention, a difluorocyclopropane compound can be produced under milder reaction conditions and with a higher conversion rate and a higher yield compared to conventional art. Further, by-products can be reduced significantly, thus allowing waste to be greatly reduced. Accordingly, the production method of the present invention is easy to implement industrially (can be employed on an industrial scale) and is thus extremely practical and useful. Moreover, it can be said that the production method of the present invention is useful also on the point that bromodifluoroacetate as the difluorocyclopropanation agent can be inexpensively and easily obtained and can be handled relatively easily (for example, sodium chlorodifluoroacetate has deliquescent properties due to moisture absorption and is difficult to be handled, whereas sodium bromodifluoroacetate does not have any deliquescent property).

BEST MODE FOR CARRYING OUT THE INVENTION

Hereinafter, the present invention will be described in detail. The scope of the present invention is not limited to the description. In addition to the following examples, the present invention can be suitably changed and then practiced within a range in which the effects of the present invention are not reduced. Note that the entire specification of Japanese Patent Application No. 2010-003201 (filed on Jan. 8, 2010), to which priority is claimed by the present application, is incorporated herein. In addition, all the publications such as prior art documents, laid-open publications, patents and other patent documents cited herein are incorporated herein by reference.

The method for producing a difluorocyclopropane compound of the present invention is characterized by using bromodifluoroacetate as a difluorocyclopropanation agent.

More specifically, the production method of the present invention is a method for producing a difluorocyclopropane compound by reacting a compound having a chain or cyclic ethylene skeleton or a derivative thereof with a difluorocyclopropanation agent, which is characterized by using bromodifluoroacetate as the difluorocyclopropanation agent as described above.

The difluorocyclopropane compound obtained by the production method of the present invention is not limited to difluorocyclopropane and includes all compounds containing a difluorocyclopropane-derived skeleton structure in the chemical structure thereof. That is, it is meant that the difluorocyclopropane compound of the present invention includes all difluorocyclopropane compounds that may be substituted with any group and derivatives of difluorocyclopropane compounds.

Specific examples of the difluorocyclopropane compound of the present invention include a compound represented by the following general formula (2):

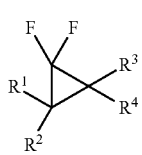

(2)

In this regard, in the general formula (2), $R^1$ to $R^4$ each independently represent, for example, a hydrogen atom, or a $C_{1-10}$ linear or branched aliphatic hydrocarbon group, aromatic ring group, alkoxy group, alkoxycarbonyl group, trialkylsilyl group or boryl group, which may be substituted with any group, but there is no limitation thereon.

The "aliphatic hydrocarbon group" may be saturated or unsaturated, and examples thereof include, but are not limited to, an alkyl group, an alkenyl group, an alkynyl group and an unsaturated aliphatic hydrocarbon group having two or more carbon-carbon unsaturated double bonds and/or triple bonds. Further, in the "aliphatic hydrocarbon group", hydrogen atoms bound to any carbon atoms of the hydrocarbon group may be each independently substituted with any number and any combination of groups selected from, for example, a halogen atom, a $C_{1-10}$ linear or branched alkoxy group, a $C_{1-10}$ linear or branched haloalkoxy group, a $C_{1-10}$ linear or branched alkylamino group, a $C_{1-10}$ linear or branched alkylthio group, a cyano group, an aminocarbonyl group ($CONH_2$), an aromatic ring group, a nucleic-acid base, an aromatic ring oxy group, an aliphatic heterocyclic group, a protector of a hydroxyl group, a protector of an amino group, and a protector of a carboxyl group, etc.

Examples of the "aromatic ring group" include, but are not limited to, aromatic hydrocarbon groups such as a phenyl group, a naphthyl group and an anthryl group, and aromatic heterocyclic groups containing an oxygen atom, a nitrogen atom, a sulfur atom or the like such as a furyl group, a pyrrolyl group, a thienyl group, a benzofuryl group, an indolyl group and a benzothienyl group. Further, these aromatic hydrocarbon groups and aromatic heterocyclic groups may be substituted with a group selected from, for example, a $C_{1-10}$ linear or branched alkyl group, a halogen atom, a $C_{1-10}$ linear or branched haloalkyl group, a $C_{1-10}$ linear or branched alkoxy group, a $C_{1-10}$ linear or branched haloalkoxy group, a $C_{1-10}$ linear or branched alkylamino group, a $C_{1-10}$ linear or branched alkylthio group, a cyano group, an aminocarbonyl group, an unsaturated group, an aromatic ring group, an aromatic ring oxy group, an aliphatic heterocyclic group, a protector of a hydroxyl group, a protector of an amino group, and a protector of a carboxyl group, etc.

Examples of the "alkoxy group" include, but are not limited to, a $C_{1-10}$ linear or branched alkoxy group, an aromatic ether group, a trialkylsiloxy group and an acyloxy group.

Examples of the "alkoxycarbonyl group" include, but are not limited to, an alkoxycarbonyl group consisting of a $C_{1-10}$ linear or branched alkoxy group.

Examples of the "trialkylsilyl group" include, but are not limited to, a trimethylsilyl group and a triethylsilyl group.

Examples of the "boryl group" include, but are not limited to, a di(alkoxy) boryl group and a dialkylboryl group.

Regarding the aforementioned substituents, examples of the "halogen atom" include atoms of fluorine, chlorine, bromine, iodine, etc. Examples of the "$C_{1-10}$ linear or branched alkoxy group" include a methoxy group, an ethoxy group and a propoxy group. Examples of the "$C_{1-10}$ linear or branched haloalkoxy group" include a fluoromethoxy group, a chloromethoxy group and a bromomethoxy group. Examples of the "$C_{1-10}$ linear or branched alkylamino group" include a dimethylamino group, a diethylamino group and a dipropylamino group. Examples of the "$C_{1-10}$ linear or branched alkylthio group" include a methylthio group, an ethylthio group and a propylthio group. Examples of the "nucleic-acid base" include an adenine residue, a guanine residue, a hypoxanthine residue, a xanthine residue, an uracil residue, a thymine residue and a cytosine residue. Examples of the "aromatic ring oxy group" include a phenoxy group and a naphthoxy group. Examples of the "aliphatic heterocyclic group" include a piperidyl group, a piperidino group and a morpholinyl group. As the "protector of a hydroxyl group, protector of an amino group and protector of a carboxyl group", for example, protecting groups described in Protective Groups in Organic Synthesis, Third Edition, 1999, John Wiley & Sons, Inc., etc. may be used. Specifically, examples of the "protector of a hydroxyl group" include a trityl group (triphenylmethyl group), a tetrahydropyranyl group (THP group) and a tetrahydrofuranyl group (THF group). Examples of the "protector of an amino group" include a benzyloxycarbonyl group, a tert-butoxycarbonyl (Boc) group, a 9-fluorenylmethoxycarbonyl (Fmoc) group, a 3-nitro-2-pyridinesulfenyl (Npys) group and a p-methoxybenzyloxycarbonyl [Z(MeO)] group. Examples of the "protector of a carboxyl group" include a methyl (Me) group, an ethyl (Et) group, a tert-butyl (t-Bu) group, a trichloroethyl (Tce) group, a phenacyl (Pac) group, a benzyl (Bzl) group, a 4-nitrobenzyl [Bzl (4-$NO_2$)] group and a 4-methoxybenzyl [Bzl (4-MeO)] group.

Further, among $R^1$ to $R^4$ in the general formula (2), $R^2$ and $R^4$ (or $R^1$ and $R^3$) may mutually constitute a portion of the same aliphatic ring. Specific examples of such embodiments include those in which each of $R^2$ and $R^4$ is the aforementioned aliphatic hydrocarbon group (particularly the alkyl group) and any carbon atoms in the respective hydrocarbon groups bind to each other to constitute a portion of a ring structure, thus constituting an aliphatic ring. In another embodiment, $R^2$ and $R^4$ may mutually constitute a portion of the same aliphatic heterocycle. Examples of the aliphatic heterocycle include those having a cyclic skeleton in which a part of carbon atoms constituting a cyclic skeleton of the above-described aliphatic ring have been substituted with nitrogen atoms or oxygen atoms.

In addition, $R^2$ and $R^4$ (or $R^1$ and $R^3$) may mutually form a single bond.

In the structural formula represented by the general formula (2), among carbon atoms constituting a cyclopropane ring, carbon atoms other than those to which 2 fluorine atoms are bound may be asymmetric carbon atoms, but there is no limitation thereon. Further, in the general formula (2), $R^2$ and $R^4$ (or $R^1$ and $R^3$) may mutually form a single bond. In this case, specific examples thereof include a compound represented by the general formula (2') below. It can be said that the compound represented by the general formula (2') is a derivative of the difluorocyclopropane compound represented by the general formula (2).

(2')

In addition, $R^2$ and $R^4$ (or $R^1$ and $R^3$) in the general formula (2) may mutually constitute a portion of the same aliphatic ring. Specific examples of such embodiments include those in which each of $R^2$ and $R^4$ is the aforementioned aliphatic hydrocarbon group (particularly the alkyl group) and any carbon atoms in the respective hydrocarbon groups bind to each other to constitute a portion of a ring structure, thus constituting an aliphatic ring. Compounds represented by general formula (2") below, etc. can be exemplified. It can be said that the compounds represented by general formula (2"), etc. are derivatives of difluorocyclopropane compounds represented by general formula (2). Note that in the general formula (2") below, it is preferred that $R^2$ and $R^4$ are, for example, each independently a methylene group which may be substituted with any group.

(2")

In another embodiment, $R^2$ and $R^4$ (or $R^1$ and $R^3$) in the general formula (2) may mutually constitute a portion of the same aliphatic heterocycle. Examples of the aliphatic heterocycle include those having a cyclic skeleton in which a part of carbon atoms constituting a cyclic skeleton of the above-described aliphatic ring have been substituted with a nitrogen atom or an oxygen atom.

Specific preferred examples of the compound represented by the general formula (2) and its derivative (including those represented by the general formulae (2') and (2")) include various difluorocyclopropane compounds produced in the working examples described later.

The difluorocyclopropane compound and its derivative obtained by the production method of the present invention are preferably an optically-active substance and a meso body, but are not limited thereto.

Examples of the compound having a chain or cyclic ethylene skeleton (carbon-carbon unsaturated double bond) to be used as a raw material compound in the production method of the present invention include, but are not limited to, all chain or cyclic compounds including an ethylene skeleton (skeleton structure derived from an ethylene group) in the chemical structure thereof and derivative compounds thereof.

Examples of the compound having an ethylene skeleton in the present invention include a compound represented by the following general formula (1):

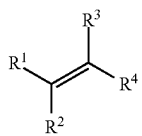

(1)

In the general formula (1), $R^1$ to $R^4$ are the same as above (that is, they are the same as those described in the explanation of the general formula (2)).

Further, in the general formula (1), $R^2$ and $R^4$ (or $R^1$ and $R^3$) may mutually form a single bond. In this case, specific examples thereof include a compound represented by the general formula (1') below. The compound represented by the general formula (1') is a compound having an acetylene skeleton (carbon-carbon unsaturated triple bond) obtained as a result of the formation of a single bond by $R^2$ and $R^4$, and it can be said that the compound is a derivative of the compound having an ethylene skeleton represented by the general formula (1).

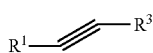

(1')

In addition, $R^2$ and $R^4$ (or $R^1$ and $R^3$) in the general formula (1) may mutually constitute a portion of the same aliphatic ring. Specific examples of such embodiments include those in which each of $R^2$ and $R^4$ is the aforementioned aliphatic hydrocarbon group (particularly the alkyl group) and any carbon atoms in the respective hydrocarbon groups bind to each other to constitute a portion of a ring structure, thus constituting an aliphatic ring. Compounds represented by general formula (1") below, etc. can be exemplified. It can be said that the compounds represented by the general formula (1"), etc. are derivatives of difluorocyclopropane compounds represented by general formula (1). Note that in the general formula (1") below, it is preferred that $R^2$ and $R^4$ are, for example, each independently a methylene group which may be substituted with any group.

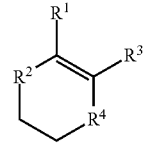

(1")

In another embodiment, $R^2$ and $R^4$ (or $R^1$ and $R^3$) in the general formula (1) may mutually constitute a portion of the same aliphatic heterocycle. As described above, examples of the aliphatic heterocycle include those having a cyclic skeleton in which a part of carbon atoms constituting a cyclic skeleton of the above-described aliphatic ring have been substituted with a nitrogen atom or an oxygen atom.

Specific preferred examples of the compound represented by the general formula (1) and its derivative (including those represented by the general formulae (1') and (1")) include various compounds having an ethylene skeleton to be used in the working examples described later.

Specific examples of bromodifluoroacetate to be used as a raw material compound as before in the production method of the present invention include those represented by the following formula:

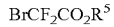

$BrCF_2CO_2R^5$

In the above-described formula, $R^5$ is preferably an alkali metal atom or alkali earth metal atom. Preferred examples of the alkali metal atom include sodium, lithium and potassium, and preferred examples of the alkali earth metal include magnesium.

Bromodifluoroacetate generates difluorocarbene in a reaction system and has the difluorocyclopropanation action on the aforementioned compound having an ethylene skeleton or its derivative.

In the production method of the present invention, conditions for a reaction between the compound having an ethylene skeleton or its derivative and bromodifluoroacetate are not limited, but for example, conditions described below are preferred.

That is, a reaction solvent may be a solvent having a high boiling point (approximately 150° C. or higher) generally used for organic chemical synthesis, and there is no limitation thereon, but for example, diglyme, N,N-dimethylformamide, N-methylpyrrolidone, etc. are preferably used.

The amount of the reaction solvent to be used is not particularly limited, but may be 0.1 L (liter) or more, generally preferably 0.1 to 20 L, and particularly preferably 0.1 to 10 L for 1 mol of the compound represented by the general formula (1) or its derivative. These organic solvents can be used solely or in combination.

The blending ratio of the raw material compound may be suitably set depending on the type of a compound used, and there is no limitation thereon. For example, bromodifluoroacetate is used in an amount of preferably 1 to 10 equivalents, and more preferably 1.2 to 8 equivalents of the compound represented by the general formula (1) or its derivative.

The reaction temperature of the reaction is, for example, preferably 100 to 200° C., and more preferably 120 to 180° C.

The reaction time of the reaction may vary depending on the type of a substrate, reaction conditions, etc., and therefore there is no particular limitation thereon. For example, the reaction time is preferably 5 to 60 minutes, more preferably 5 to 30 minutes, and even more preferably 10 to 20 minutes. Note that the end point of the reaction is preferably a point when it is recognized that the raw material has almost disappeared by following the reaction progress by an analysis means such as gas chromatography, liquid chromatography and NMR.

The pressure condition of the reaction is not particularly limited, and for example, the pressure may be provided in the range of ordinary pressure (0.1 MPa (absolute pressure standard, the same applies to the following)) to 2 MPa, and in this case, it is preferably in the range of 0.1 MPa to 1.5 MPa, and particularly preferably in the range of 0.1 MPa to 1 MPa.

The reactor to be used in this step may be any reactor which can provide a reaction under ordinary pressure or increased pressure. When a reaction is performed under increased pressure, materials of the reactor are not particularly limited as long as they are pressure-proof, and a reactor lined with tetrafluoroethylene resin, chlorotrifluoroethylene resin, vinylidene fluoride resin, PFA resin, glass or the like, or a glass container may be used. Note that the reaction may be performed with inert gas being introduced into the reactor. Preferred examples of the inert gas to be used include nitrogen gas and argon gas.

The post-treatment method is not particularly limited, and the treatment of a product after the reaction is completed may be carried out based on a usual treatment method of organic synthesis (e.g., extraction, distillation and dehydration). A difluorocyclopropane compound can be obtained by a usual means.

The production method of the present invention is at an advantage in terms of cost and productivity because it allows a reaction at a lower temperature condition (mild reaction condition) compared to the conventional method for synthesizing a difluorocyclopropane compound, and a difluorocyclopropane compound as a target product can be obtained with a high conversion rate. Since a target product can be thus obtained with a high conversion rate, isolation/purification of the target product from the reaction system, which was difficult for the conventional synthesis method, becomes easy, and as a result, the target product can be obtained with a significantly high yield.

Further, in the production method of the present invention, by using bromodifluoroacetate as the difluorocyclopropanation agent, for example, the drip rate of the difluorocyclopropanation agent at the time of the reaction may be increased compared to the conventional method. Since the difluorocyclopropane compound as the target product can be synthesized in a shorter time for this reason, the production method of the present invention is excellent in productivity.

Note that the difluorocyclopropane compound and its derivative obtained by the production method of the present invention are useful, for example, as a biologically active agent, its synthetic intermediate or the like of medicaments, pesticides, etc., since they have an atomic group and an atom which can impart 2 specific properties of a cyclopropane ring and a fluorine atom. Further, in the field of material science, for example, use as a crystal or a raw material thereof may be considered.

Hereinafter, the present invention will be specifically described by way of illustrative examples, but the present invention is not limited thereto.

Note that in the below-described working examples (including comparative examples), reactions were performed under an inert gas atmosphere (under argon or nitrogen atmosphere).

Further, as dry diglyme to be used as a reaction solvent, a commercialized product (Aldrich) was used.

The measurement of $^1$H NMR and $^{19}$F NMR was carried out using JEOL JNM-LA ($^1$H NMR: 400 MHz, $^{19}$F NMR: 376 MHz), and as a measurement solvent, deuterochloroform (CDCl$_3$) was used. The chemical shift δ (ppm) of $^1$H NMR was obtained based on tetramethylsilane (TMS, δ 0 ppm), and the chemical shift δ (ppm) of $^{19}$F NMR was obtained based on hexafluorobenzene (C$_6$F$_6$, δ 0 ppm). GC/MS was measured using Thermo TRACE GC ULTRA.

EXAMPLES

Example 1

Preparation of Sodium Bromodifluoroacetate

Sodium bromodifluoroacetate, which is a raw material compound and also a difluorocyclopropanation agent, was prepared by reacting bromodifluoroacetic acid and sodium hydroxide as shown in the following reaction formula:

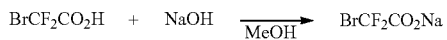

Specifically, sodium hydroxide (1.1 g, 27.5 mmol) was dissolved in methanol (12.5 ml), and a methanol solution of bromodifluoroacetic acid (4.8 g, 27.5 mmol) was slowly added dropwise to the mixture with stirring at 0° C., and after that, the mixture was stirred at room temperature for 2 hours. When the reaction solution was concentrated, then dried and weighed, sodium bromodifluoroacetate as a colorless solid (4.8 g, 24.3 mmol) was obtained with a yield of 88%. The sodium bromodifluoroacetate obtained in this working example was used in all the other working examples described below.

Synthesis of 1,1-difluoro-2,2-diphenylchloropropane (Compound 2a)

Compound 2a was prepared as shown by the reaction formula below:

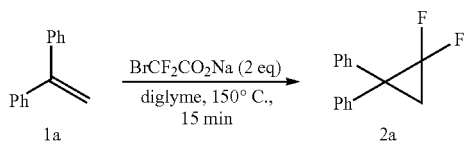

Specifically, 1,1-diphenylethylene (Compound 1a; 54.0 mg, 0.3 mmol) and diglyme (1.5 mL) were put into a two-neck evacuation flask under nitrogen atmosphere, and a diglyme (3.0 mL) solution of sodium bromodifluoroacetate (118 mg, 0.6 mmol) was added dropwise to the mixture at 150° C. for 10 minutes, and then the mixture was stirred for 5 minutes. The solution after the reaction was subjected to GC/MS measurement, and it was found that targeted Compound 2a was produced with a conversion yield of 99%. When sodium chlorodifluoroacetate (ClCF$_2$CO$_2$Na) was used instead of sodium bromodifluoroacetate for comparison, targeted Compound 2a was produced with a conversion yield of 64%. The reaction mixture was washed with water, and then dried with sodium sulfate. The solvent was distilled away under reduced pressure, and then the residue was purified by silica gel column chromatography (developing solvent was hexane:EtOAc=100:1), thereby obtaining targeted Compound 2a as a colorless solid with an isolation yield of 82% (57.3 mg).

Compound 2a:

Mp 50-51° C.; $^1$H NMR (CDCl$_3$) δ 2.08 (t, J$_{HF}$=8.6 Hz, 2H), 7.24 (t, J=7.6 Hz, 2H), 7.32 (t, J=7.6 Hz, 4H), 7.41 (d,

J=7.6 Hz, 4H); $^{19}$F NMR (CDCl$_3$) δ 31.8 (d, J$_{HF}$=8.6 Hz, 2F); GC/MS m/z (%) 230 (M$^+$, 80), 210 (80), 178 (39), 165 (100), 77 (16)

Example 2

Synthesis of 1-(tert-butyl)-4-(2,2-difluorocyclopropyl)benzene (Compound 2b)

Compound 2b was prepared as shown by the reaction formula below:

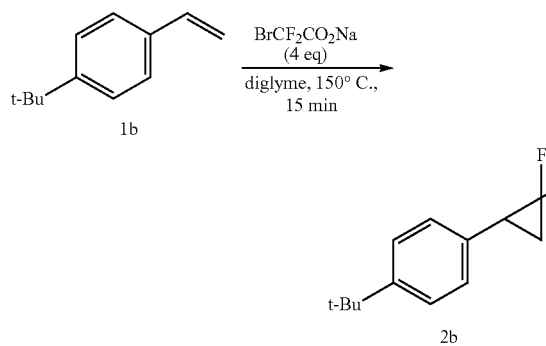

Specifically, 1-tert-butyl-4-vinylbenzene (Compound 1b; 16.0 mg, 0.1 mmol) and diglyme (0.5 mL) were put into a two-neck evacuation flask under nitrogen atmosphere, and a diglyme (1.0 mL) solution of sodium bromodifluoroacetate (78.7 mg, 0.4 mmol) was added dropwise to the mixture at 150° C. for 10 minutes, and then the mixture was stirred for 5 minutes. The solution after the reaction was subjected to GC/MS measurement, and it was found that targeted Compound 2b was produced with a conversion yield of 100%. When sodium chlorodifluoroacetate was used instead of sodium bromodifluoroacetate for comparison, targeted Compound 2b was produced with a conversion yield of 61%. The reaction mixture was washed with water, and then dried with sodium sulfate. The solvent was distilled away under reduced pressure, and then $^1$H NMR and $^{19}$F NMR of the residue (15.9 mg) were measured.

Compound 2b:
$^1$H NMR (CDCl$_3$) δ 1.31 (s, 9H), 1.60 (dddd, J$_{HF}$=12.8, 3.8 Hz, J$_{HH}$=8.0, 7.0 Hz, 1J), 1.79 (dddd, J$_{HF}$=12.6, 5.0 Hz, J$_{HH}$=12.0, 7.7 Hz, 1H), 2.72 (ddd, J$_{HF}$=13.2 Hz, J$_{HH}$=12.0, 8.0 Hz, 1H), 7.16 (d, J=8.4 Hz, 2H), 7.35 (d, J=8.4 Hz, 2H); $^{19}$F NMR (CDCl$_3$) δ 19.3 (dd, J$_{FF}$=152 Hz, J$_{HF}$=12.8 Hz, 1F), 35.8 (ddd, J$_{FF}$=152 Hz, J$_{HF}$=13.2, 12.6 Hz, 1F); GC/MS m/z (%) 210 (M$^+$, 1), 195 (22), 145 (17), 77 (20), 57 (100).

Example 3

Synthesis of 1-butyl-4-(3,3-difluorocyclopropyrenyl)benzene (Compound 2c)

Compound 2c was prepared as shown by the reaction formula below:

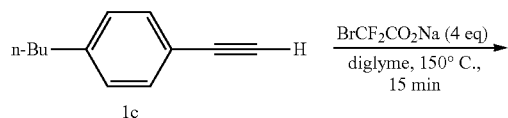

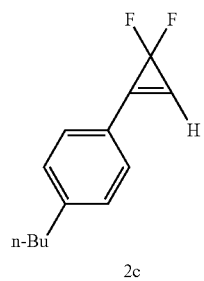

Specifically, 1-butyl-4-ethynyl-benzene (Compound 1c; 15.8 mg, 0.1 mmol) and diglyme (0.5 mL) were put into a two-neck evacuation flask under nitrogen atmosphere, and a diglyme (1.0 mL) solution of sodium bromodifluoroacetate (78.7 mg, 0.4 mmol) was added dropwise to the mixture at 150° C. for 10 minutes, and then the mixture was stirred for 5 minutes. The solution after the reaction was subjected to GC/MS measurement, and it was found that targeted Compound 2c was produced with a conversion yield of 98%. When sodium chlorodifluoroacetate was used instead of sodium bromodifluoroacetate for comparison, targeted Compound 2c was produced with a conversion yield of 56%. The reaction mixture was washed with water, and then dried with sodium sulfate. The solvent was distilled away under reduced pressure, and then $^1$H NMR and $^{19}$F NMR of the residue (19.5 mg) were measured.

Compound 2c:
$^1$H NMR (CDCl$_3$) δ 0.94 (t, J=7.2 Hz, 3H), 1.3-1.4 (m, 2H), 1.64 (quint, J=7.2 Hz, 2H), 2.70 (t, J=7.2 Hz, 2H), 7.2-7.3 (m, 1H), 7.36 (d, J=8.4 Hz, 2H), 7.78 (d, J=8.4 Hz, 2H); $^{19}$F NMR (CDCl$_3$) δ 55.3 (s, 2F); GC/MS m/z (%) 208 (M$^+$, 48), 165 (100), 151 (18), 115 (92).

Example 4

Synthesis of rac-[(1S,3S)-2,2-difluoro-3-phenylcyclopropyl]methyl acetate (Compound 2d)

Compound 2d was prepared as shown by the reaction formula below:

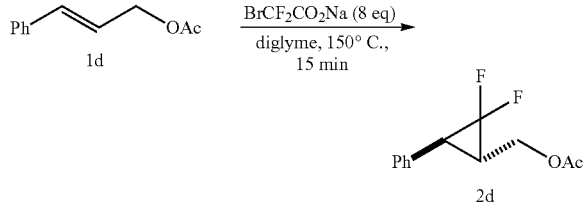

Specifically, cinnamyl acetate (Compound 1d; 52.8 mg, 0.3 mmol) and diglyme (1.5 mL) were put into a two-neck evacuation flask under nitrogen atmosphere, and a diglyme (3.0 mL) solution of sodium bromodifluoroacetate (472 mg, 2.4 mmol) was added dropwise to the mixture at 150° C. for 10 minutes, and then the mixture was stirred for 5 minutes. The solution after the reaction was subjected to GC/MS measurement, and it was found that targeted Compound 2d was produced with a conversion yield of 93%. When sodium chlorodifluoroacetate was used instead of sodium bromodifluoroacetate for comparison, targeted Compound 2d was produced with a conversion yield of 35%. The reaction mixture was washed with water, and then dried with sodium sulfate. The solvent was distilled away under reduced pressure, and then the residue was purified by silica gel column chromatography (developing solvent was hexane: EtOAc=50:1), thereby obtaining targeted Compound 2d that was colorless and oily with an isolation yield of 73% (49.5 mg).

Compound 2d:

$^1$H NMR (CDCl$_3$) δ 2.10 (s, 3H), 2.27 (dddd, $^3J_{HF}$=13.6 Hz, $J_{HH}$=7.7, 7.6, 7.5 Hz, 1H), 2.66 (dd, $^3J_{HF}$=14.6 Hz, $J_{HH}$=7.6 Hz, 1H), 4.25 (ddd, $^4J_{HF}$=1.5 Hz, $J_{HH}$=12.0, 7.7 Hz, 1H), 4.36 (dddd, $^4J_{HF}$=2.2, 1.0 Hz, $J_{HH}$=12.0, 7.6 Hz, 1H), 7.22 (d, J=6.8 Hz, 2H), 7.3-7.4 (m, 3H); $^{19}$F NMR (CDCl$_3$) δ 24.4 (dd, 1F, $J_{FF}$=158 Hz, $J_{HF}$=13.6 Hz), 26.3 (dd, 1F, $J_{FF}$=158 Hz, $J_{HF}$=14.6 Hz); GC/MS m/z (%) 166 (100).

Example 5

Synthesis of 1,1-difluoro-1,2-diphenylcyclopropane (Compound 2e)

Compound 2e was prepared as shown by the reaction formula below:

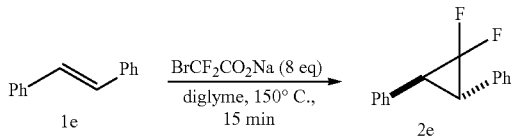

Specifically, 1,2-diphenylethylene (Compound 1e; 18.0 mg, 0.1 mmol) and diglyme (0.5 mL) were put into a two-neck evacuation flask under nitrogen atmosphere, and a diglyme (1.0 mL) solution of sodium bromodifluoroacetate (157 mg, 0.8 mmol) was added dropwise to the mixture at 150° C. for 10 minutes, and then the mixture was stirred for 5 minutes. The solution after the reaction was subjected to GC/MS measurement, and it was found that targeted Compound 2e was produced with a conversion yield of 34%. When sodium chlorodifluoroacetate was used instead of sodium bromodifluoroacetate for comparison, targeted Compound 2e was produced with a conversion yield of 6%. The reaction mixture was washed with water, and then dried with sodium sulfate. The solvent was distilled away under reduced pressure, and then $^1$H NMR and $^{19}$F NMR of the residue were measured.

Compound 2e:

$^1$H NMR (CDCl$_3$) δ 3.04 (t, $J_{HF}$=7.6 Hz, 2H), 7.3-7.4 (m, 6H), 7.41 (d, J=7.8 Hz, 4H); $^{19}$F NMR (CDCl$_3$) δ 27.7 (d, $J_{HF}$=7.6 Hz, 2F); GC/MS m/z (%) 230 (M$^+$, 16), 210 (71), 178 (47), 165 (28), 152 (100), 133 (74), 89 (51), 77 (26).

Example 6

Synthesis of benzyl 2,2-difluoro-1-methyl-1-cyclopropanecarboxylate (Compound 2f)

Compound 2f was prepared as shown by the reaction formula below:

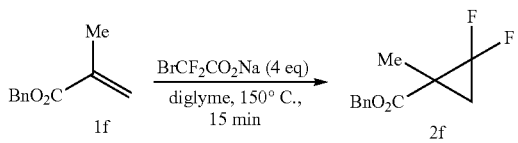

Specifically, benzyl methacrylate (Compound 1f; 52.8 mg, 0.3 mmol) and diglyme (1.5 mL) were put into a two-neck evacuation flask under nitrogen atmosphere, and a diglyme (3.0 mL) solution of sodium bromodifluoroacetate (236 mg, 1.2 mmol) was added dropwise to the mixture at 150° C. for 10 minutes, and then the mixture was stirred for 5 minutes. The solution after the reaction was subjected to GC/MS measurement, and it was found that targeted Compound 2f was produced with a conversion yield of 99%. When sodium chlorodifluoroacetate was used instead of sodium bromodifluoroacetate for comparison, targeted Compound 2f was produced with a conversion yield of 66%. The reaction mixture was washed with water, and then dried with sodium sulfate. The solvent was distilled away under reduced pressure, and then the residue was purified by silica gel column chromatography (developing solvent was hexane: EtOAc=50:1), thereby obtaining targeted Compound 2f that was colorless and oily with an isolation yield of 84% (57.0 mg).

Compound 2f:

$^1$H NMR (CDCl$_3$) δ 1.34 (ddd, $^3J_{HF}$=11.4 Hz, $^4J_{HF}$=5.0 Hz, $J_{HH}$=7.6 Hz, 1H), 1.46 (s, 3H), 2.2-2.3 (m, 1H), 5.1-5.2 (m, 2H), 7.3-7.4 (m, 5H); $^{19}$F NMR (CDCl$_3$) δ 25.1 (dd, $J_{FF}$=150 Hz, $^3J_{HF}$=11.4, 1F), 26.6 (dd, $J_{FF}$=150 Hz, $^3J_{HF}$=9.4 Hz, 1F); GC/MS m/z (%) 91 (100).

Example 7

Synthesis of (2,2-difluoro-1-phenylcyclopropoxy)trimethylsilane (Compound 2g)

Compound 2g was prepared as shown by the reaction formula below:

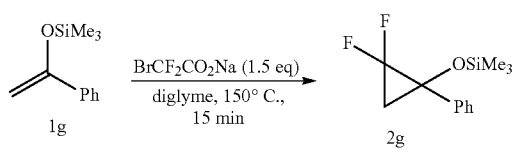

Specifically, (1-phenylvinyloxy)-trimethylsilane (Compound 1g; 192 mg, 1.0 mmol) and diglyme (3.2 mL) were put into a two-neck evacuation flask under nitrogen atmosphere, and a diglyme (3.2 mL) solution of sodium bromodifluoroacetate (295 mg, 1.5 mmol) was added dropwise to the mixture at 150° C. for 10 minutes, and then the mixture was stirred for 5 minutes. The reaction mixture was washed with water, and then dried with sodium sulfate. The solvent was distilled away under reduced pressure, and then the residue was purified by silica gel column chromatography (hexane: EtOAc=50:1), thereby obtaining targeted Compound 2g that was colorless and oily with an isolation yield of 54% (130 mg, 0.54 mmol).

Compound 2g:

$^1$H NMR (CDCl$_3$) δ 0.02 (s, 9H), 1.72 (ddd, $J_{HF}$=15.8, 5.4 Hz, $J_{HH}$=8.9 Hz, 1H), 1.89 (ddd, $J_{HF}$=15.6, 6.0 Hz, $J_{HH}$=8.9 Hz, 1H), 7.3-7.5 (m, 5H); $^{19}$F NMR (CDCl$_3$) δ 23.1 (dd, $J_{FF}$=153 Hz, $J_{HF}$=15.8, 1F), 28.7 (dd, $J_{FF}$=153 Hz, $J_{HF}$=15.6, 1F); GC/MS m/z (%) 241 (100), 227 (2), 177 (18), 149 (41), 105 (53), 73 (85).

Example 8

Synthesis of (7,7-difluorobicyclo[4.1.0]hepto-1-yloxy)trimethylsilane (Compound 2h)

Compound 2h was prepared as shown by the reaction formula below:

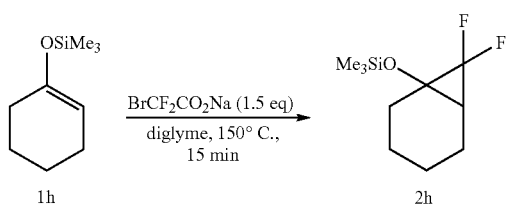

Specifically, (cyclohexa-1-enyloxy)trimethylsilane (Compound 1h; 17.0 mg, 0.1 mmol) and diglyme (0.5 mL) were put into a two-neck evacuation flask under nitrogen atmosphere, and a diglyme (1.0 mL) solution of sodium bromodifluoroacetate (29.5 mg, 0.15 mmol) was added dropwise to the mixture at 150° C. for 10 minutes under nitrogen atmosphere, and then the mixture was stirred for 5 minutes. The solution after the reaction was subjected to $^{19}$F NMR analysis (a reference substance was TFE), and it was found that targeted Compound 2h that was colorless and oily was produced with a conversion yield of 96%. The reaction mixture was washed with water, and then dried with sodium sulfate. The solvent was distilled away under reduced pressure, and then $^{1}$H NMR and $^{19}$F NMR of the residue (24.4 mg) were measured.

Compound 2h:
$^{1}$H NMR (CDCl$_3$) δ 0.17 (s, 9H), 1.2-1.4 (m, 4H), 1.4-1.6 (m, 2H), 1.8-2.0 (m, 2H), 2.1-2.2 (m, 1H); $^{19}$F NMR (CDCl$_3$) δ 15.4 (d, J$_{FF}$=154 Hz, 1F), 25.9 (dd, J$_{FF}$=154 Hz, J$_{HF}$=15.0, 1F); GC/MS m/z (%) 220 (M$^+$, 2), 205 (7), 81 (31), 73 (100).

Example 9

Synthesis of (1,1-difluorobicyclo[4.1.0]hepto-2-phenyl)cyclopropane (Compound 2l)

Compound 2l was prepared as shown by the reaction formula below:

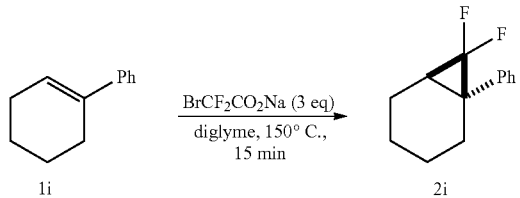

Specifically, 1-phenyl-1-cyclohexene (Compound 1i; 47.8 mg, 0.30 mmol) and diglyme (3.0 mL) were put into a two-neck evacuation flask under nitrogen atmosphere, and a diglyme (3.0 mL) solution of sodium bromodifluoroacetate (178.4 mg, 0.90 mmol) was added dropwise to the mixture at 150° C. for 10 minutes, and then the mixture was stirred for 5 minutes. The solution after the reaction was subjected to GC/MS measurement, and it was found that targeted Compound 2l was produced with a conversion yield of 99%. The reaction mixture was washed with water, and then dried with sodium sulfate. The solvent was distilled away under reduced pressure, and then the residue was purified by silica gel column chromatography (developing solvent was hexane: EtOAc=50:1), thereby obtaining targeted Compound 2l that was colorless and oily with an isolation yield of 80% (50.2 mg).

Compound 2l:
$^{1}$H NMR (CDCl$_3$) δ 1.28-1.52 (m, 4H), 1.72-1.88 (m, 3H), 1.94-2.06 (m, 1H), 2.10-2.22 (m, 1H), 7.21-7.36 (m, 5H); $^{19}$F NMR (CDCl$_3$) δ 18.7 (d, J$_{FF}$=150 Hz, 1F), 33.9 (dd, J$_{FF}$=150 Hz, J$_{HF}$=15.0, 1F); GC/MS m/z (%) 208 (M$^+$, 100), 77 (20).

Example 10

Synthesis of 1-chloro-4-(1,1-difluoro-2-methylcyclopropyl)benzene (Compound 2j)

Compound 2j was prepared as shown by the reaction formula below:

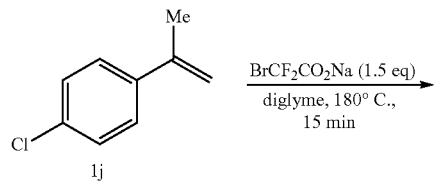

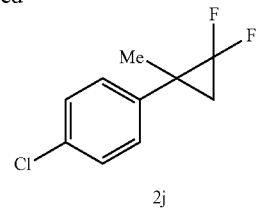

Specifically, 4-chloro-α-methylstyrene (1j, 46.7 mg, 0.3 mmol) and diglyme (3.0 mL) were put into a two-neck evacuation flask under nitrogen atmosphere, and a diglyme (3.0 mL) solution of sodium bromodifluoroacetate (88.6 mg, 0.45 mmol) was added dropwise to the mixture at 180° C. for 10 minutes, and then the mixture was stirred for 5 minutes. The solution after the reaction was subjected to GC/MS measurement, and it was found that targeted Compound 2j was produced with a conversion yield of 99%. The reaction mixture was washed with water, and then dried with sodium sulfate. The solvent was distilled away under reduced pressure, and then the residue was purified by silica gel column chromatography (developing solvent was hexane: EtOAc=30:1), thereby obtaining targeted Compound 2j that was colorless and oily with an isolation yield of 79% (49.1 mg).

Compound 2j:
$^{1}$H NMR (CDCl$_3$) δ 1.48-1.54 (m, 3H), 1.41 (ddd, J$_{HF}$=12.0, 4.4 Hz, J$_{HH}$=8.0 Hz, 1H), 1.63 (ddd, J$_{HF}$=13.6, 4.0 Hz, J$_{HH}$=8.0 Hz, 1H), 7.24 (d, J=8.4 Hz, 2H), 7.31 (d, J=8.4 Hz, 2H); $^{19}$F NMR (CDCl$_3$) δ 24.1 (dd, J$_{FF}$=150 Hz, J$_{HF}$=13.6, 1F), 29.2 (dd, J$_{FF}$=150 Hz, J$_{HF}$=12.0, 1F); GC/MS m/z (%) 201 (M-1$^+$, 1), 187 (14), 167 (100), 152 (6), 147 (38), 75 (6).

Example 11

Synthesis of 1,1-difluoro-2,3-diphenylcycloprop-2-ene (Compound 2k)

Compound 2k was prepared as shown by the reaction formula below:

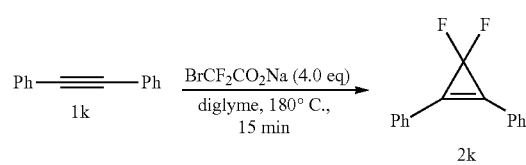

Specifically, diphenylacetylene (Compound 1k; 53.5 mg, 0.3 mmol) and diglyme (3.0 mL) were put into a two-neck evacuation flask under nitrogen atmosphere, and a diglyme (3.0 mL) solution of sodium bromodifluoroacetate (236.4 mg, 1.20 mmol) was added dropwise to the mixture at 180° C. for 10 minutes, and then the mixture was stirred for 5 minutes. The solution after the reaction was subjected to GC/MS measurement, and it was found that targeted Compound 2k was produced with a conversion yield of 99%. The reaction mixture was washed with water, and then dried with sodium sulfate. The solvent was distilled away under reduced pressure, and then the residue was purified by recrystallization (solvent: hexane-EtOAc), thereby obtaining targeted Compound 2k that was colorless and solid with an isolation yield of 75% (51.7 mg).

Compound 2k:

Mp 44-46° C.; $^1$H NMR (CDCl$_3$) δ 7.47-7.57 (m, 6H), 7.79 (d, 4H, J=7.8 Hz); $^{19}$F NMR (CDCl$_3$) δ 49.5 (s, 2F); GC/MS m/z (%) 228 (M$^+$, 90), 227 (96), 207 (25), 178 (100), 151 (18), 76 (8).

Example 12

Synthesis of 2-(2,2-difluoro-1-phenylcyclopropyl)-4,4,5,5-tetramethyl-1,3,2-dioxaborolane (Compound 21)

Compound 21 was prepared as shown by the reaction formula below:

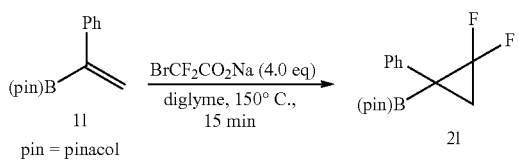

Specifically, 1-phenyl-vinylboronic acid pinacol ester (Compound 11; 71.5 mg, 0.3 mmol) and diglyme (3.0 mL) were put into a two-neck evacuation flask under nitrogen atmosphere, and a diglyme (3.0 mL) solution of sodium bromodifluoroacetate (236.2 mg, 1.20 mmol) was added dropwise to the mixture at 150° C. for 10 minutes, and then the mixture was stirred for 5 minutes. The solution after the reaction was subjected to GC/MS measurement, and it was found that targeted Compound 21 was produced with a conversion yield of 99%. The reaction mixture was washed with water, and then dried with sodium sulfate. The solvent was distilled away under reduced pressure, and then the residue was purified by silica gel column chromatography (developing solvent was hexane: EtOAc=50:1), thereby obtaining targeted Compound 21 that was a pale yellow solid with an isolation yield of 67% (58.1 mg).

Compound 21:

Mp 97-99° C.; $^1$H NMR (CDCl$_3$) δ 7.33-7.21 (m, 5H), 2.06 (dd, J$_{HF}$=12.0 Hz, J$_{HH}$=6.4 Hz, 1H), 1.70 (ddd, J$_{HF}$=12.0, 2.4 Hz, J$_{HH}$=6.4 Hz, 1H), 1.23 (s, 6H), 1.19 (s, 6H); $^{19}$F NMR (CDCl$_3$) δ 36.6 (dd, J$_{FF}$=142.9 Hz, J$_{HF}$=12.0 Hz, 1F), 29.6 (dd, J$_{FF}$=142.9 Hz, J$_{HF}$=12.0 Hz, 1F); GC/MS m/z (%) 280 (M$^+$, 4), 133 (10), 115 (13), 83 (100).

Comparative Example 1

In Comparative Example 1, as the difluorocyclopropanation agent, instead of sodium bromodifluoroacetate used in the Examples above, sodium chlorodifluoroacetate (ClCF$_2$CO$_2$Na) was used (the same applies to the other comparative examples).

Synthesis of (2,2-difluoro-1-phenylcyclopropoxy)trimethylsilane (Compound 2g)

Compound 2g was prepared as shown by the reaction formula below:

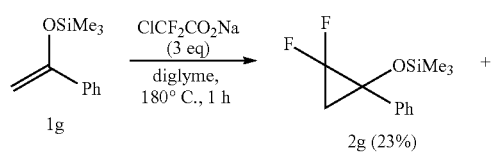

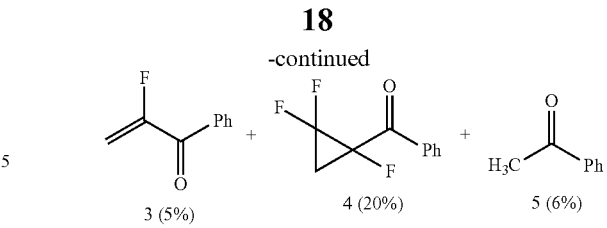

Specifically, (1-phenylvinyloxy)-trimethylsilane (Compound 1g; 61.3 mg, 0.32 mmol) and diglyme (1.0 mL) were put into a two-neck evacuation flask under nitrogen atmosphere, and a diglyme (3.0 mL) solution of sodium chlorodifluoroacetate (292 mg, 1.9 mmol) was added dropwise to the mixture at 180° C. for 55 minutes, and then the mixture was stirred for 5 minutes. The reaction mixture was washed with water, and then dried with sodium sulfate. The solvent was distilled away under reduced pressure, and then the residue was subjected to GC/MS measurement. As a result, Compound 2g, Compound 3, Compound 4 and acetophenone (Compound 5) were obtained with yields of 23%, 5%, 20% and 6%, respectively.

Compound 3:

$^1$H NMR (CDCl$_3$) δ 5.50 (dd, J$_{HF}$=8.2 Hz, J$_{HH}$=3.4 Hz, 1H), 5.58 (dd, J$_{HF}$=38.0 Hz, J$_{HH}$=3.4 Hz, 1H), 7.48 (t, J=7.6 Hz, 2H), 7.61 (t, J=7.6 Hz, 1H), 7.87 (d, 2H, J=7.6 Hz); $^{19}$F NMR (CDCl$_3$) δ 50.79 (dd, 1F, J$_{HF}$=8.2, 38.0 Hz); GC/MS m/z (%) 150 (57), 130 (4), 105 (100), 77 (60).

Compound 4:

$^1$H NMR (CDCl$_3$) δ 2.0-2.2 (m, 1H,), 2.7-2.9 (m, 1H), 7.4-8.0 (m, 5H); $^{19}$F NMR (CDCl$_3$) δ 22.2-22.8 (m, 1F), 23.8-24.4 (m, 1F), 77.2-77.6 (m, 1F); GC/MS m/z (%) 200 (100), 180 (23), 151 (28), 105 (53), 77 (51).

Comparative Example 2

Synthesis of (2,2-difluoro-1-phenylcyclopropoxy)trimethylsilane (Compound 2g)

Compound 2g was prepared as shown by the reaction formula below:

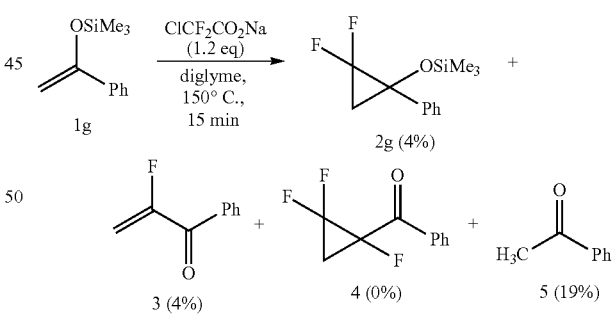

Specifically, (1-phenylvinyloxy)-trimethylsilane (Compound 1g; 61.3 mg, 0.1 mmol) and diglyme (0.5 mL) were put into a two-neck evacuation flask under nitrogen atmosphere, and a diglyme (1.0 mL) solution of sodium chlorodifluoroacetate (18.3 mg, 0.12 mmol) was added dropwise to the mixture at 150° C. for 10 minutes, and then the mixture was stirred for 5 minutes. The reaction mixture was washed with water, and then dried with sodium sulfate. The solvent was distilled away under reduced pressure, and then the residue was subjected to GC/MS measurement. As a result, Compound 2g, Compound 3 and acetophenone (Compound 5) were obtained with yields of 4%, 4% and 19%, respectively.

Comparative Example 3

Synthesis of (7,7-difluorobicyclo[4.1.0]hepto-1-yloxy)trimethylsilane (Compound 2h)

Compound 2h was prepared as shown by the reaction formula below:

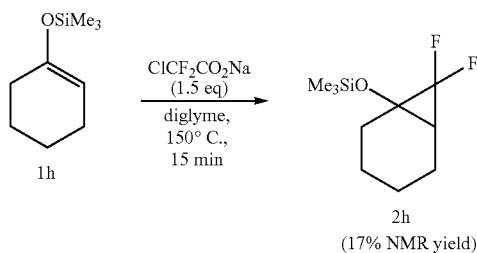

2h
(17% NMR yield)

Specifically, (cyclohexa-1-enyloxy)trimethylsilane (Compound 1h; 17.0 mg, 0.1 mmol) and diglyme (0.5 mL) were put into a two-neck evacuation flask under nitrogen atmosphere, and a diglyme (1.0 mL) solution of sodium chlorodifluoroacetate (22.8 mg, 0.15 mmol) was added dropwise to the mixture at 150° C. for 10 minutes under nitrogen atmosphere, and then the mixture was stirred for 5 minutes. The solution after the reaction was subjected to $^{19}$F NMR analysis (a reference substance was TFE), and it was found that targeted Compound 2h that was colorless and oily was produced with a conversion yield of 17%.

INDUSTRIAL APPLICABILITY

According to the present invention, a difluorocyclopropane compound can be produced under milder reaction conditions and with a higher conversion rate and a higher yield compared to conventional art. Further, by-products can be reduced significantly, thus allowing waste to be greatly reduced. Accordingly, the production method of the present invention is easy to implement industrially (can be employed on an industrial scale) and is thus extremely practical and useful. Moreover, it can be said that the production method of the present invention is useful also on the point that bromodifluoroacetate as the difluorocyclopropanation agent can be inexpensively and easily obtained and can be handled relatively easily (for example, sodium chlorodifluoroacetate has deliquescent properties due to moisture absorption and is difficult to be handled, whereas sodium bromodifluoroacetate does not have any deliquescent property).

The invention claimed is:

1. A method for producing a difluorocyclopropane compound by reacting a compound having a chain or cyclic ethylene skeleton with a difluorocyclopropanation agent, wherein bromodifluoroacetate is used as the difluorocyclopropanation agent.

2. The method according to claim 1, wherein the compound having the ethylene skeleton is a compound having the following general formula (1):

(1)

wherein in the general formula (1): $R^1$ to $R^4$ each independently represent a hydrogen atom, or a $C_{1-10}$ linear or branched aliphatic hydrocarbon group, aromatic ring group, alkoxy group, alkoxycarbonyl group, trialkylsilyl group or boryl group, which may be substituted with any group; and $R^2$ and $R^4$ may mutually constitute a portion of the same aliphatic ring or aliphatic heterocycle, or may mutually form a single bond, and wherein the difluorocyclopropane compound is a compound having the following general formula (2):

(2)

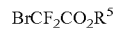

wherein in the general formula (2), $R^1$ to $R^4$ are the same as above.

3. The method according to claim 1 or 2, wherein the bromodifluoroacetate is represented by the following formula:

$BrCF_2CO_2R^5$ wherein $R^5$ represents an alkali metal atom or an alkali earth metal atom.

4. The method according to claim 3, wherein the alkali metal is sodium, lithium or potassium and the alkali earth metal is magnesium.

5. The method according to claim 1, wherein a reaction temperature of the reaction is 100 to 200° C.

6. The method according to claim 1, wherein a reaction time of the reaction is 5 to 60 minutes.

* * * * *